United States Patent [19]

Hon

[11] Patent Number: 5,497,778
[45] Date of Patent: Mar. 12, 1996

[54] APPARATUS AND METHOD FOR NONINVASIVE MEASUREMENT OF PERIPHERAL PRESSURE PULSE COMPLIANCE AND SYSTOLIC TIME INTERVALS

[76] Inventor: Edward H. Hon, 11 Bradbury Hills Rd., Bradbury, Calif. 91010

[21] Appl. No.: 85,547

[22] Filed: Jun. 30, 1993

[51] Int. Cl.$^6$ .................................................. A61B 5/021
[52] U.S. Cl. ........................ 128/672; 128/691; 128/700
[58] Field of Search .................................... 128/691, 700, 128/713, 670, 672, 689, 696, 748; 607/23

[56] References Cited

U.S. PATENT DOCUMENTS

| | | | |
|---|---|---|---|
| 2,944,542 | 7/1960 | Barnett et al. | 128/671 |
| 3,563,232 | 2/1971 | Webb | 128/715 |
| 3,608,545 | 9/1971 | Novack et al. | 128/700 |
| 3,734,086 | 5/1973 | Phelps, Sr. | 128/687 |
| 3,742,938 | 7/1973 | Stern | 128/687 |
| 3,871,360 | 3/1975 | Van Horn et al. | 128/671 |
| 4,289,141 | 9/1981 | Cormier | 128/713 |
| 4,425,922 | 1/1984 | Conti et al. | 128/700 |
| 4,442,845 | 4/1984 | Stephens | 128/687 |
| 4,446,872 | 5/1984 | Marsoner et al. | 128/700 |
| 4,510,944 | 4/1985 | Porges | 128/687 |
| 4,545,387 | 10/1985 | Balique | 128/687 |
| 4,730,619 | 3/1988 | Koning et al. | 607/23 |
| 4,802,486 | 2/1989 | Goodman et al. | 128/687 |
| 5,033,472 | 7/1991 | Sato et al. | 128/700 |
| 5,211,177 | 5/1993 | Chesney et al. | 128/713 |
| 5,238,001 | 8/1993 | Gallant et al. | 128/700 |
| 5,265,011 | 11/1993 | O'Rourke | 128/672 |

FOREIGN PATENT DOCUMENTS 0021800  1/1981  European Pat. Off. ............... 128/700

*Primary Examiner*—William E. Kamm
*Assistant Examiner*—Kennedy J. Schaetzle
*Attorney, Agent, or Firm*—Lewis Anten; Amedeo Ferraro

[57] ABSTRACT

Systolic time intervals provide a basis for the determination of total electromechanical systole and offer a physiologic approach to cardiovascular assessment. In addition, examination of the pulse wave contour changes with advancing age and hypertension suggests that these data may be useful in assessing the vascular compliance and peripheral resistance of a subject. Noninvasively obtained peripheral systolic time intervals in normal and pathologic conditions and the automated measurement and continuous plotting of several parameters, including heart rate, pulse wave arrival time, rapid ejection time, peripheral pulse wave contour, and cutaneous pressure pulse are used in assessing the subject.

4 Claims, 15 Drawing Sheets

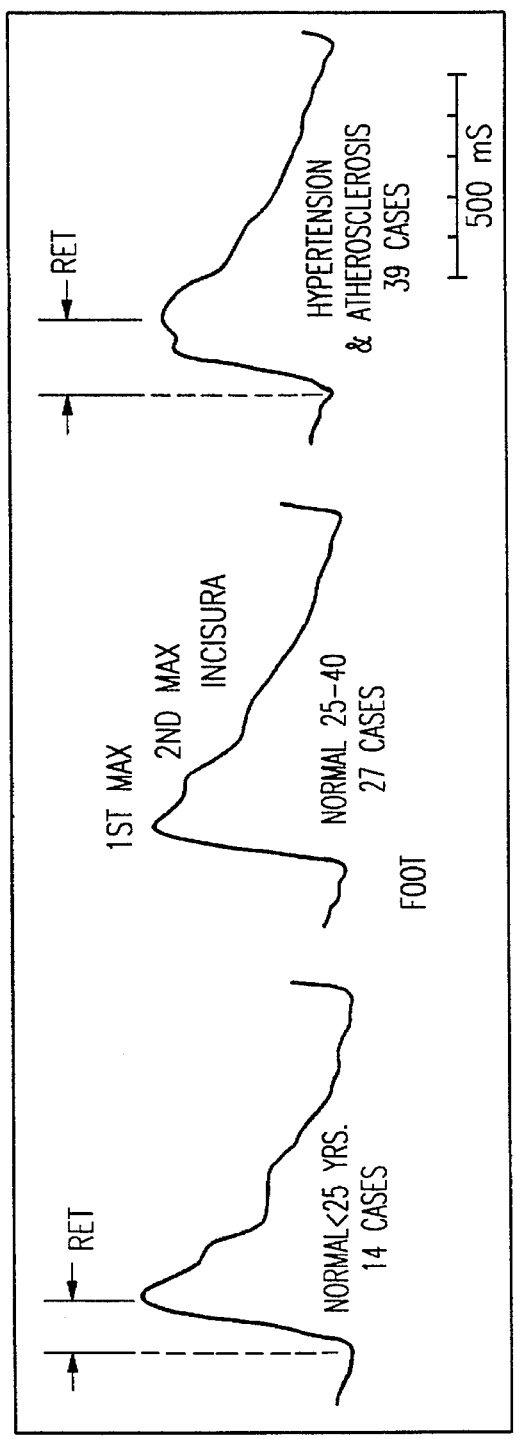
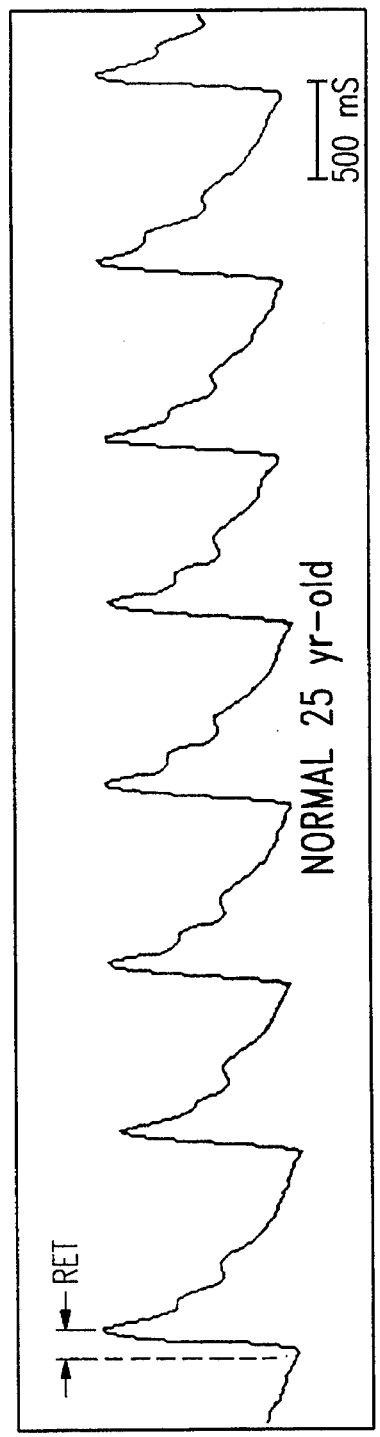
FIG. 1A CAROTID PULSE WAVES
FIG. 1B CUTANEOUS PRESSURE PULSE WAVES

CUTANEOUS
PRESSURE
PULSE WAVES

CUTANEOUS
PRESSURE
PULSE WAVES

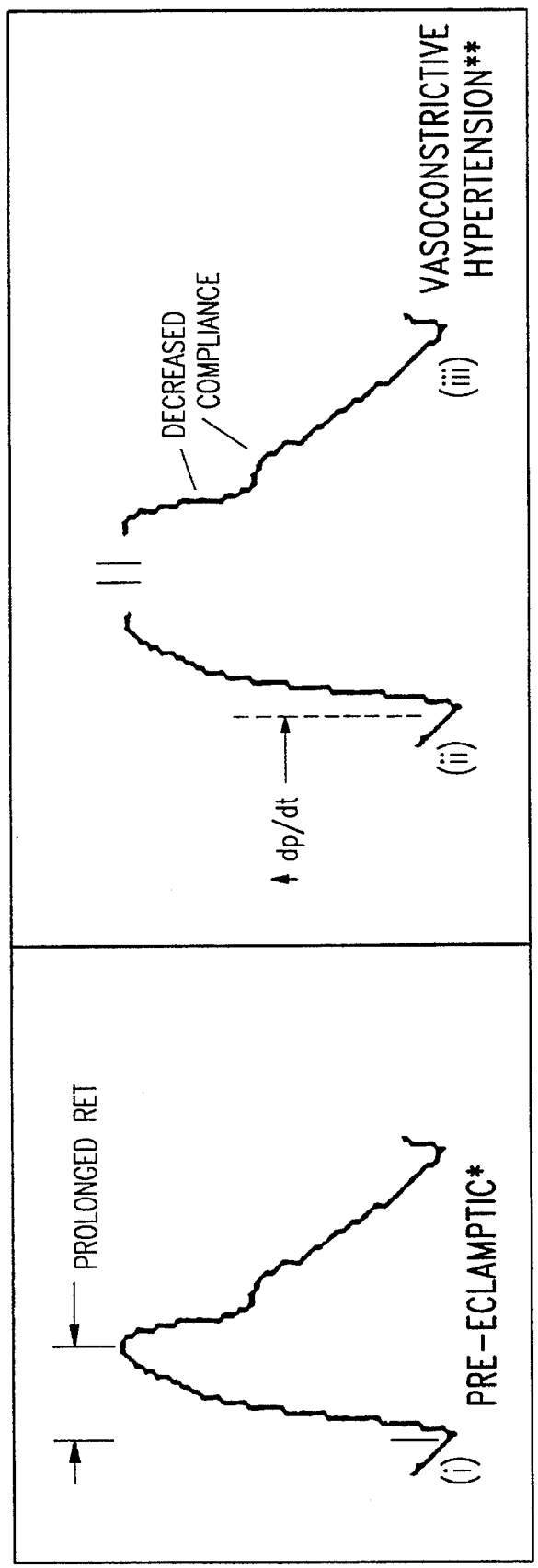

APPARATUS AND METHOD FOR NONINVASIVE MEASUREMENT OF PERIPHERAL PRESSURE PULSE COMPLIANCE AND SYSTOLIC TIME INTERVALS

BACKGROUND

Hypertension in pregnancy is associated with increased maternal and fetal morbidity and mortality. Hence, its early detection and management is essential for a good perinatal outcome. It is important to recognize that the mean arterial blood pressure at any given time is the resultant of the momentary interaction of a number of determining factors: the pumping action of the heart, cardiac output (heart rate multiplied by stroke volume), peripheral resistance (which depends on the caliber of the small arterial vessels); viscosity of the blood; quantity of blood in the arterial system; and the elasticity of vessel walls.

Measurement of blood pressure per se does not provide information about the role that each of the above causal factors may have played to determine its final magnitude. Such additional information is of importance when attempting to correct abnormal cardiovascular situations such as severe hypertension, hypotension, cardiac failure, or excessive blood loss. However, in the majority of noncatastrophic clinical situations, mean arterial blood pressure (MAP) is primarily determined by the pumping action of the heart, heart rate (HR), peripheral resistance, and the elasticity of vessel walls (since blood volume and viscosity are usually unchanged).

Currently, noninvasive techniques utilizing the carotid artery pulse have been described for assessing myocardial contractility, on which the pumping action of the heart is primarily dependent. These measurements, which are known as "systolic time intervals," are derived from simultaneous recordings of the electrocardiogram, phonocardiogram, and carotid artery pulsations and they provide a basis for indirect determination of total electromechanical systole.

While systolic time interval measurements offer a physiologic approach to cardiovascular assessment, they are not widely used due to technical difficulty in obtaining a noninvasive carotid artery pulse, unless patient movement is restricted or during short periods of breath-holding. Despite these practical problems, the physiologic basis for the use of systolic time intervals is fundamentally sound and provides, in principle, a method for assessing myocardial performance.

FIG. 14 shows carotid artery pulse wave showing contour changes with increasing age and hypertension/atherosclerosis. RET measurements also are shown.

FIGS. 1B and 1C show cutaneous (peripheral) pulse wave contour (PWC) changes in a 25-year-old and a 35-year-old normal pregnant patient showing the loss of downslope detail (decreased compliance). FIG. 1D shows cutaneous PWC recorded from a 19-year-old hypertensive pregnant patient which is similar to the carotid PWC recorded from hypertensive patients (3rd pulse, FIG. 1A), insofar that the 2nd maximum is higher than the first in both instances, thereby causing a prolongation of RET.

Peripheral vascular resistance is currently derived from invasive measurements of cardiac output and MAP. However, the invasive nature of this technique sharply limits its use in the prenatal patient.

Observations of the waveforms of noninvasively recorded carotid artery pulses indicate that the pulse wave contours change with advancing age and hypertension. In either situation, there is a decrease in arterial compliance and an increase in peripheral resistance. Moreover, Berne and Levy observed that "the heart is unable to eject its stroke volume into a rigid arterial system as rapidly as into a more complaint system. As compliance diminishes, peak arterial pressure occurs progressively later in systole."

From the foregoing, it is clear that although methods are available for assessing the determinants of arterial blood pressure, their clinical use is limited by the difficulties of noninvasevely obtaining a carotid artery pulse; even then the data can be acquired for only a few seconds.

SUMMARY OF THE INVENTION

The apparatus described in this application uses cutaneous blood pressure pulse (cPP), which is acquired from the finger tip with a simple-to-use pressure transducer, instead of the carotid artery pulse. The fingertip pressure transducer is disclosed in U.S. Pat. No. 4,993,422, issued on Feb. 19, 1991 to Hon et al. and is incorporated herein by reference. The PWC of these peripheral blood pressure pulses are similar to those obtained from the carotid artery and provides the basis for the development of peripheral systolic time interval measurements.

BRIEF DESCRIPTION OF THE DRAWINGS

FIG. 1A shows carotid artery pulse wave forms.

FIGS. 1B and 1C show peripheral PWC changes in a 25-year-old and 35-year-old normal pregnant patient.

FIGS. 3A–D show illustrations of four distinct types of peripheral PWCs observed in specific clinical situations. FIG. A: Recorded from a normal pregnant patient. FIGS. BI–III, CI–III, and DI–III: Recorded from hypertensive patients.

| | |
|---|---|
| HR | heart rate |
| PWAT | pulse wave arrival time (in milliseconds, mS) |
| RET | rapid ejection time (in mS) |
| cPP | cutaneous (peripheral) pressure pulse in mmHg |
| cPP wave | peripheral pressure PWC. |

Figure 6A:
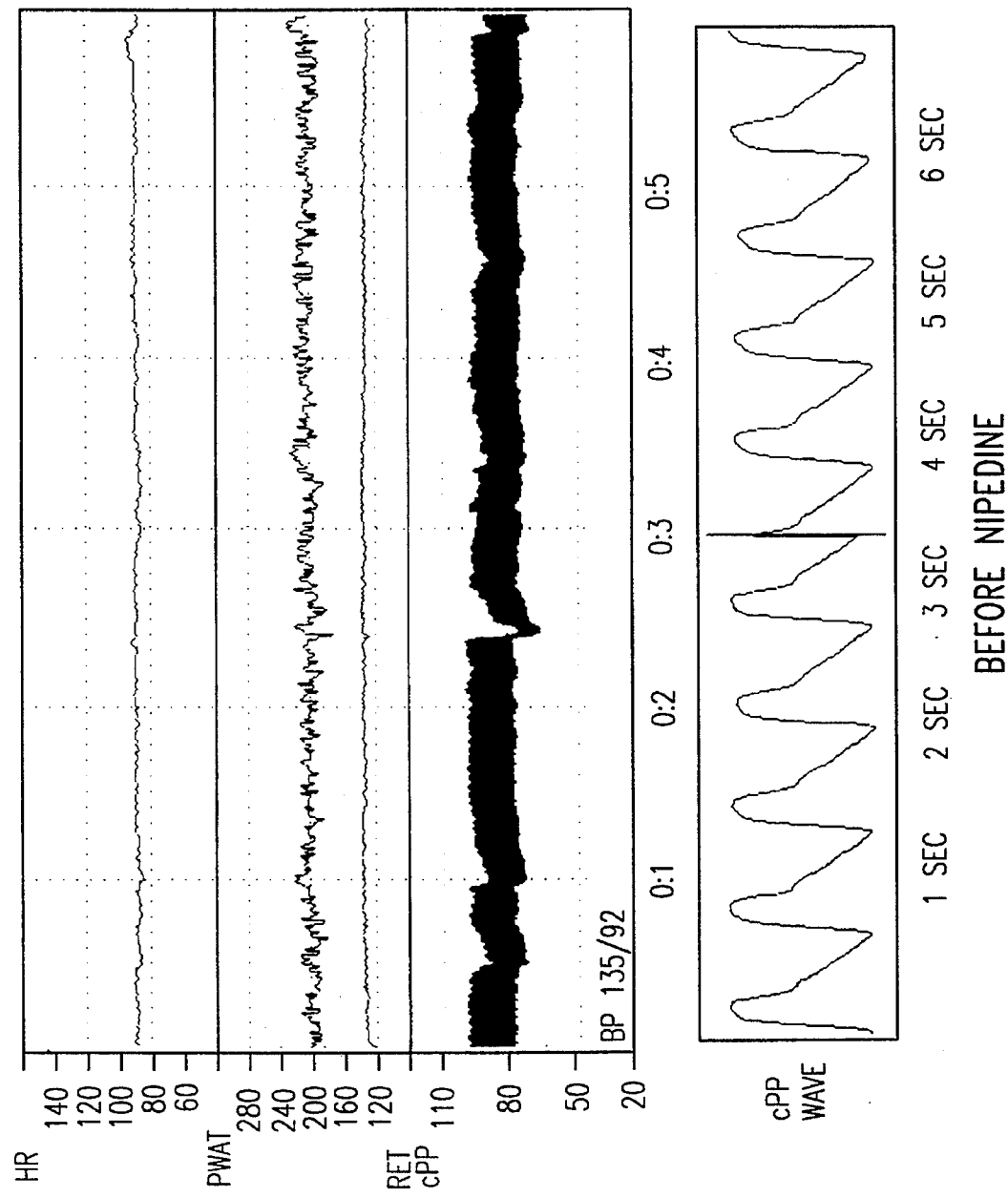
Figure 6B:
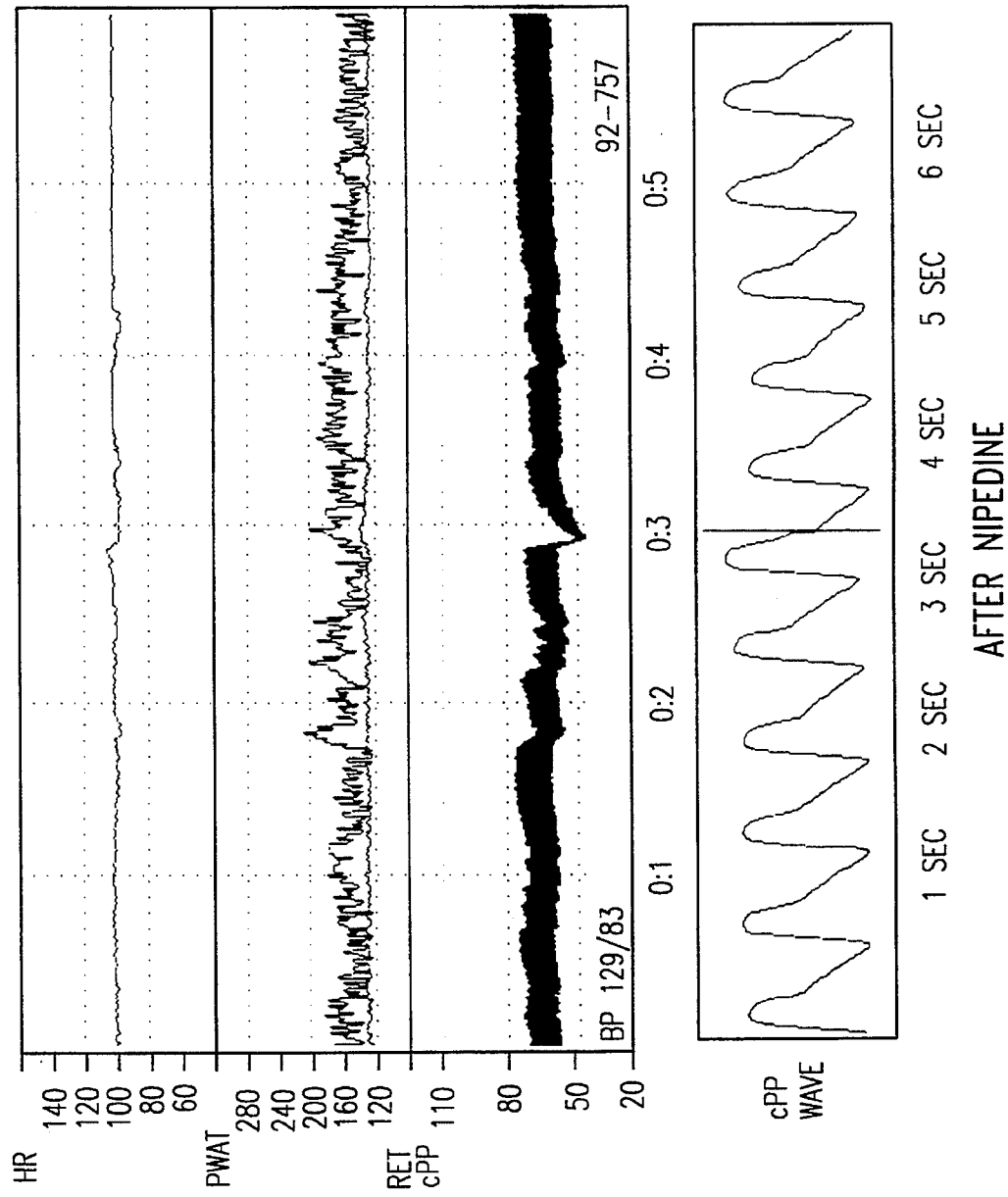

FIGS. 6A and 6B show cardiovascular changes recorded during the administration of a calcium-blocking agent (nifedipine) in a patient with borderline hypertension. The recordings were made for 71 min following sublingual administration of the drug.

Figure 7:
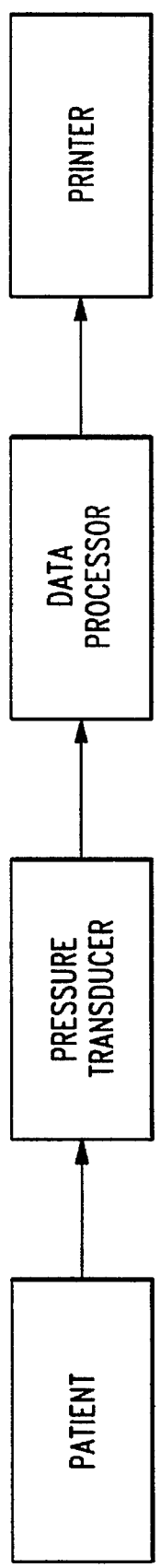

FIG. 7 is a schematic illustration of the apparatus associated with the measurement of arterial compliance of a patient.

DETAILED DESCRIPTION OF THE DRAWINGS

The systolic time intervals are used in cardiology are composed of two intervals:
1. Pre-ejection period (PEP): composed of the QRS depolarization time plus isovolumic contraction time (ICT), i.e., the interval from mitral valve closure (MC) to aortic valve opening (Ao).
2. Left ventricular ejection time (LVET): interval from the foot of the pulse to the incisura, i.e. from aortic valve opening (Ao) to closure (Ac).

The interval can be further subdivided into a rapid ejection phase to peak pulse pressure; and a reduced ejection phase (from the peak of the pulse to incisura).

Figure 1C:
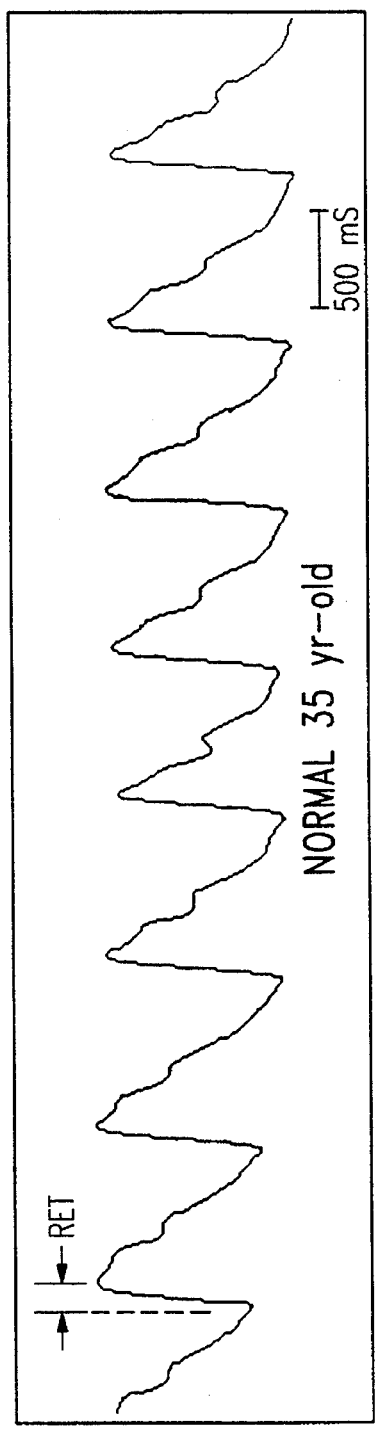
Figure 1D:
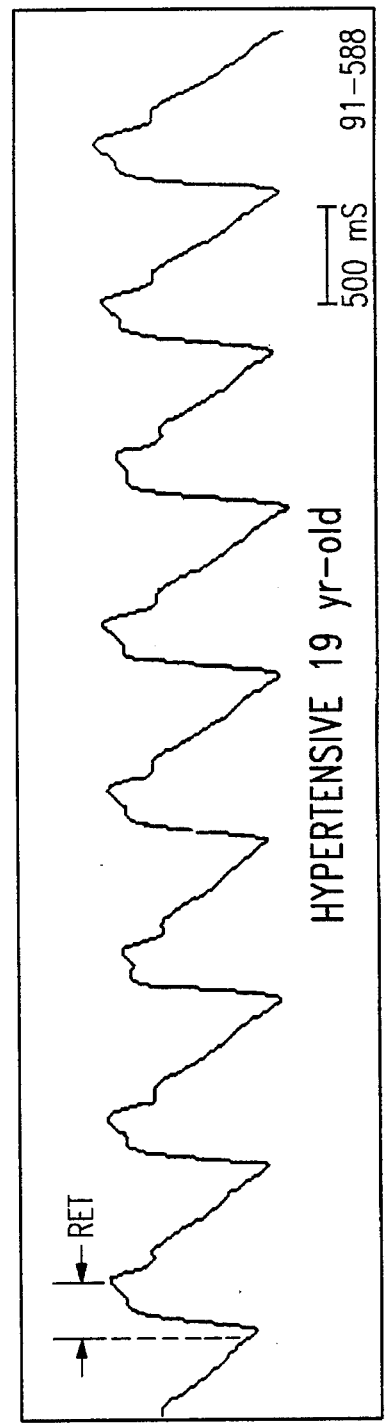
FIG. 1D shows peripheral PWC changes in a 19-year-old hypertensive patient.
Figure 2A:
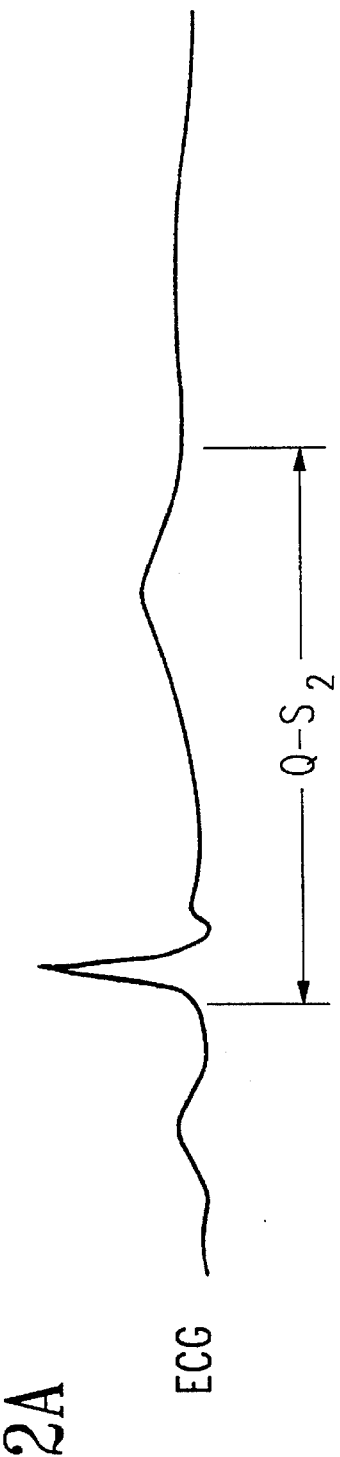
FIGS. 2A–B show periphreal pressure pulse and systolic time intervals.
Figure 2B:
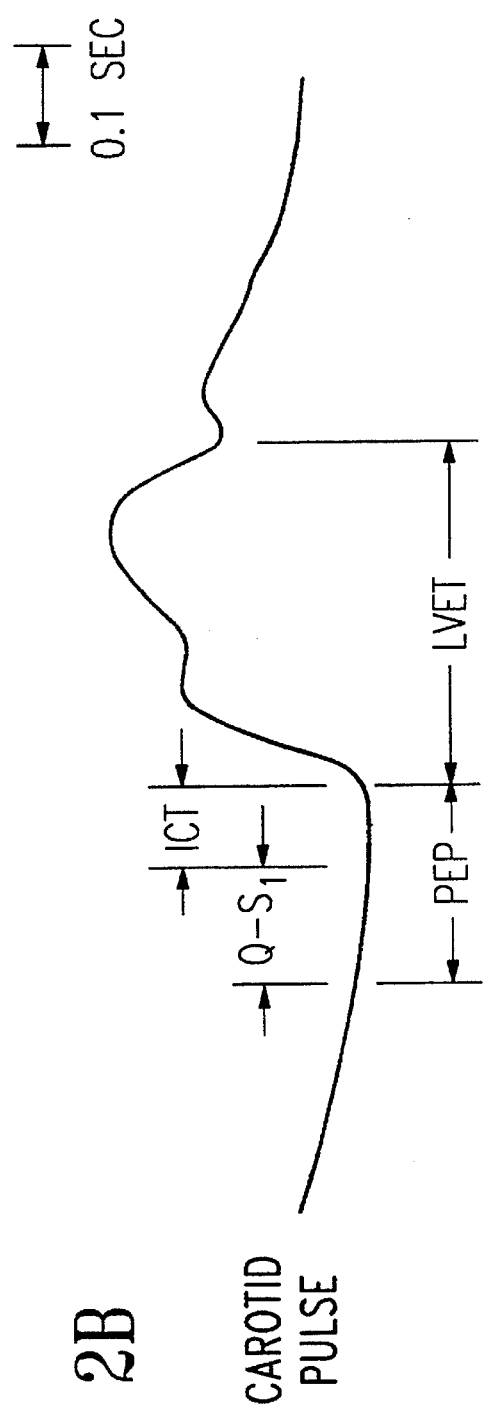

In the textbook discussions of systolic time intervals, an aortic or carotid artery pulse has been used for measuring the various intervals (FIGS. 2A–B). When the intervals are computed from a peripheral pulse instead of an aortic or carotid pulse, the following differences should be noted: The electromechanical interval (EMI) in the peripheral system is measured from the peak of the R-wave of the electrocardiogram (ECO) to the onset of the peripheral pulse; this interval is analogous to the ICT. In addition to this interval, EMI includes the pulse wave travelling time (PWTT). These two intervals, ICT and PWTT, together make up the pulse wave arrival time (PWAT). PWAT differs from PEP since it includes PWTT but omits QRS depolarization time. PEP omits PWTT, since systolic time intervals are derived from a central pulse. LVET in the peripheral systolic time interval system is analogous to that of the central system. Also being measured is the analog of the duration of the rapid ejection phase of the aortic pressure pulse and labeling the rapid ejection time (RET).

MATERIALS AND METHODS INSTRUMENTATION

The data acquisition, processing and display systems have been described in detail previously. Briefly, the cutaneous pressure pulse transducer is applied over the distal phalanx of a finger of one hand ECG electrodes are attached to another finger and to the suprasternal area. The cPP transducer and ECG electrodes are plugged into a data processing unit connected to a laptop computer and a printer.

PWAT and RET Computations

A special microcomputer running at 11 MHz concurrently computes PWAT and RET. Data sampling is done at a rate of 2 milliseconds (mS) and the analog-to-digital conversion uses a 12-bit resolution. The ECG R-wave is located with a peak detector algorithm and the elapsed time from this point to the slope upturn of the cPP is determined. This interval is the PWAT. The RET is computed from the onset of the cPP slope upturn (then end-point of PWAT) to the peak of the cPP pulse.

RESULTS—Illustrative Examples

Figure 3A:
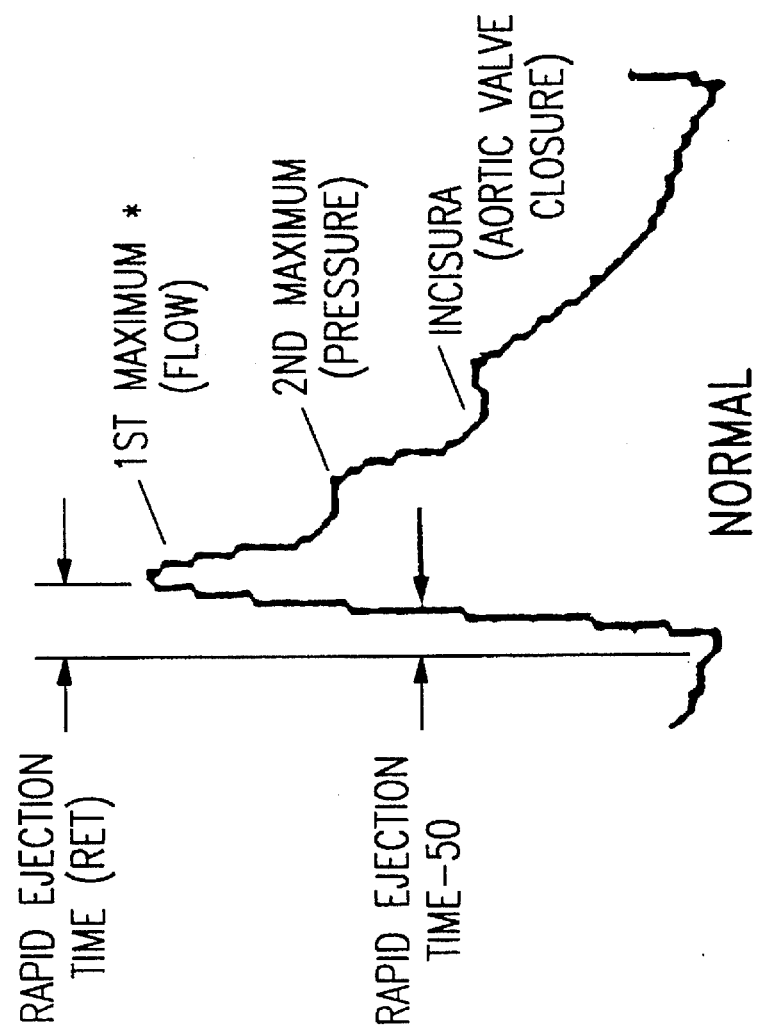
Figure 3B:
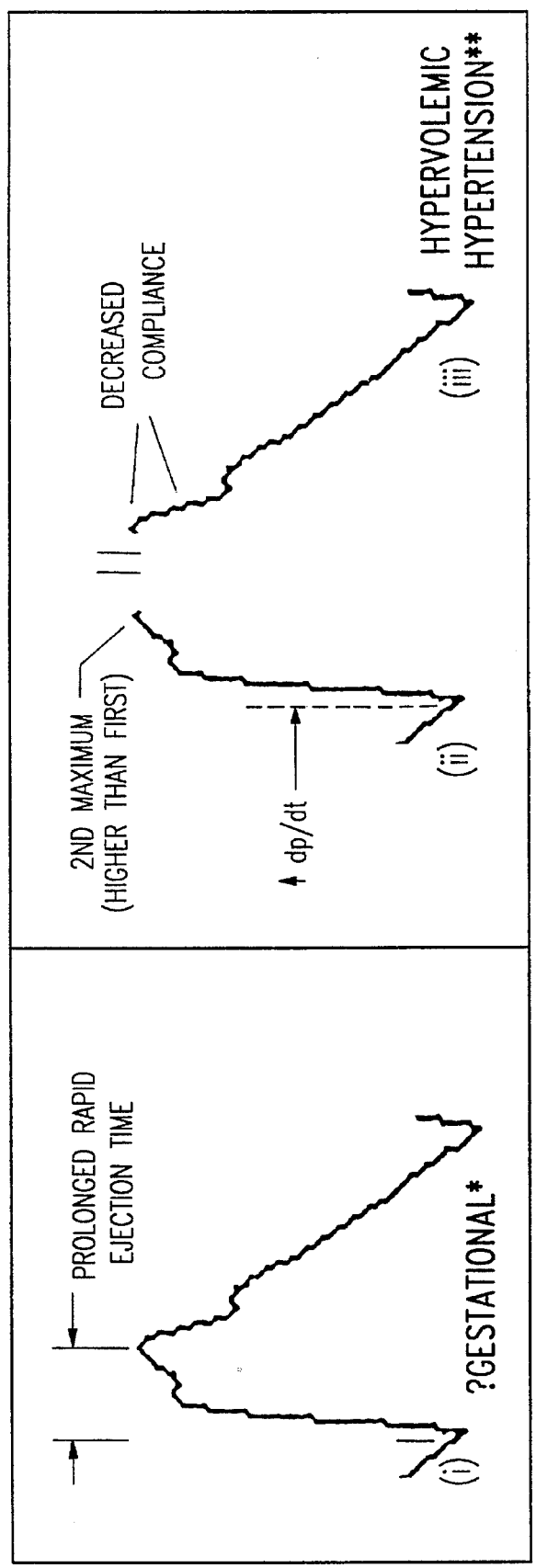
Figure 3D:
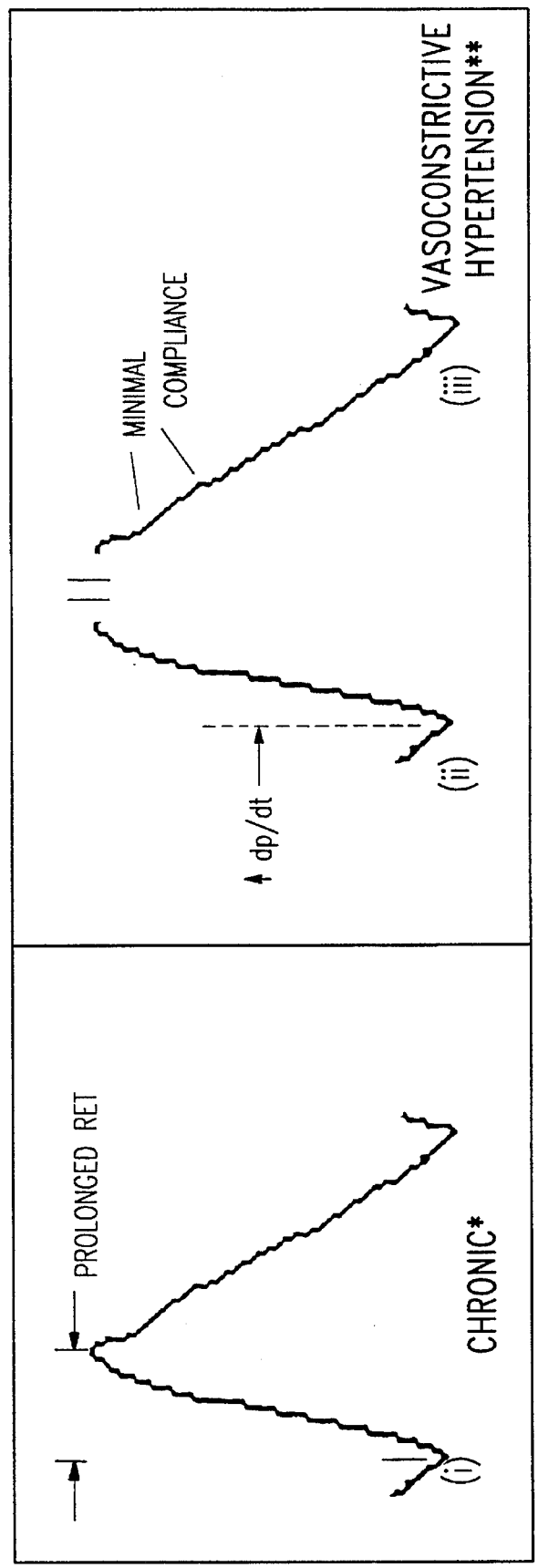

FIGS. 3A–D illustrates four different types of peripheral PWCs observed with normal (FIG. 3A) and hypertensive patients (FIGS. 3B–D). In FIG. 3A, the labeling is based on the description of similar carotid pulse details as designated by Freis and co-workers. The RET measurement is in accordance with the Berne and Levy observation concerning peak pressure; RET-50 is introduced by the author as a simple way to estimate dP/dT.

With hypertension (FIGS. 3B–D), RET is markedly prolonged (especially with chronic hypertension). Note also the differences in dP/dt and the compliance between hypervolemia, pre-eclamptic, and chronic hypertension. FIGS. 3Bi, 3Ci, and 3Di are PWCs before their upslopes (FIGS. 3Bii, 3Cii, and 3Dii have been separated from the down slopes (FIGS. 3Biii, 3Ciii, and 3Diii).

Figure 4A:
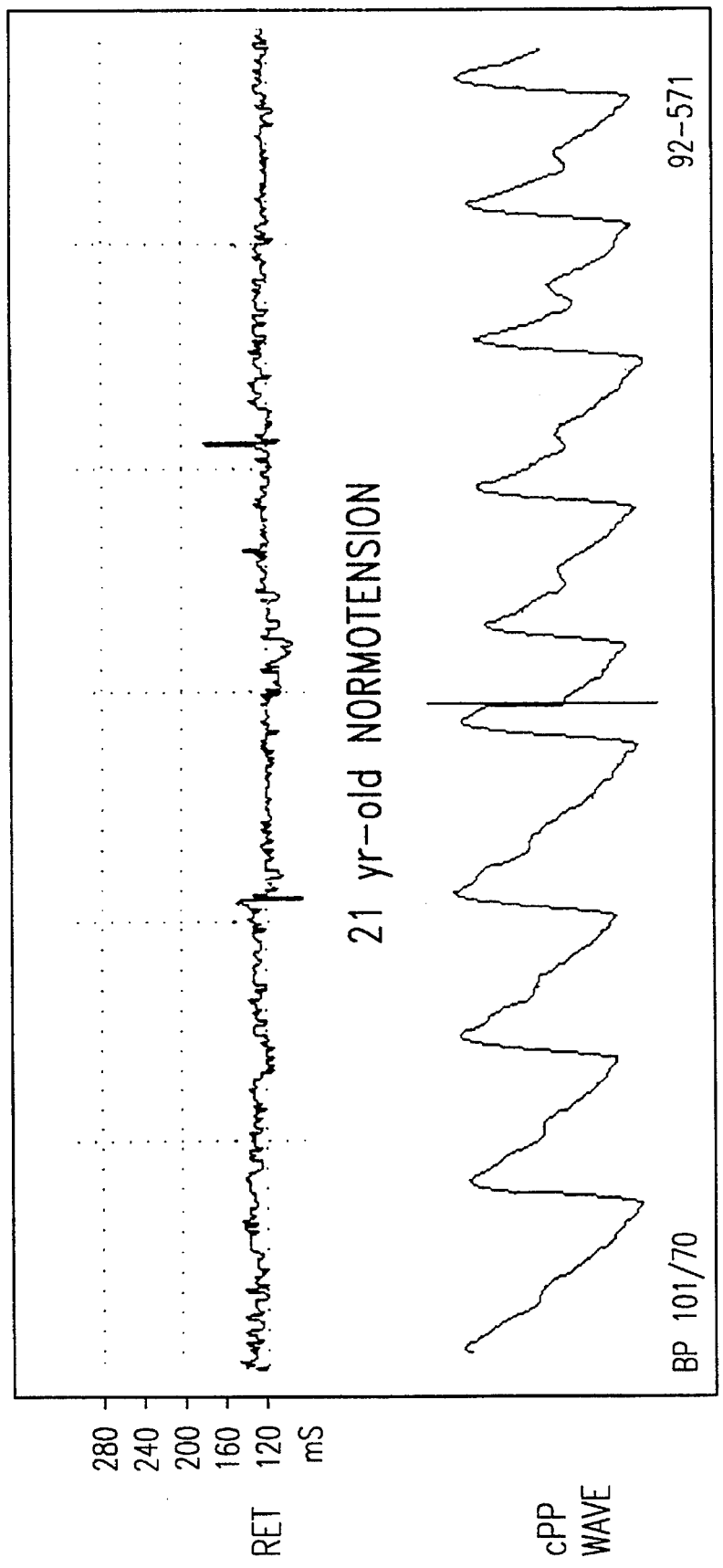
FIGS. 4A–C show increase in RET and change in peripheral PWC with advancing age. The vertical dotted lines in the upper portion of the records correspond to 1-min intervals. The first part of the PWC record in all figures (before the dark vertical line) recorded with the patient sitting: the second half (after the vertical line) was recorded with the patient standing.
Figure 4B:
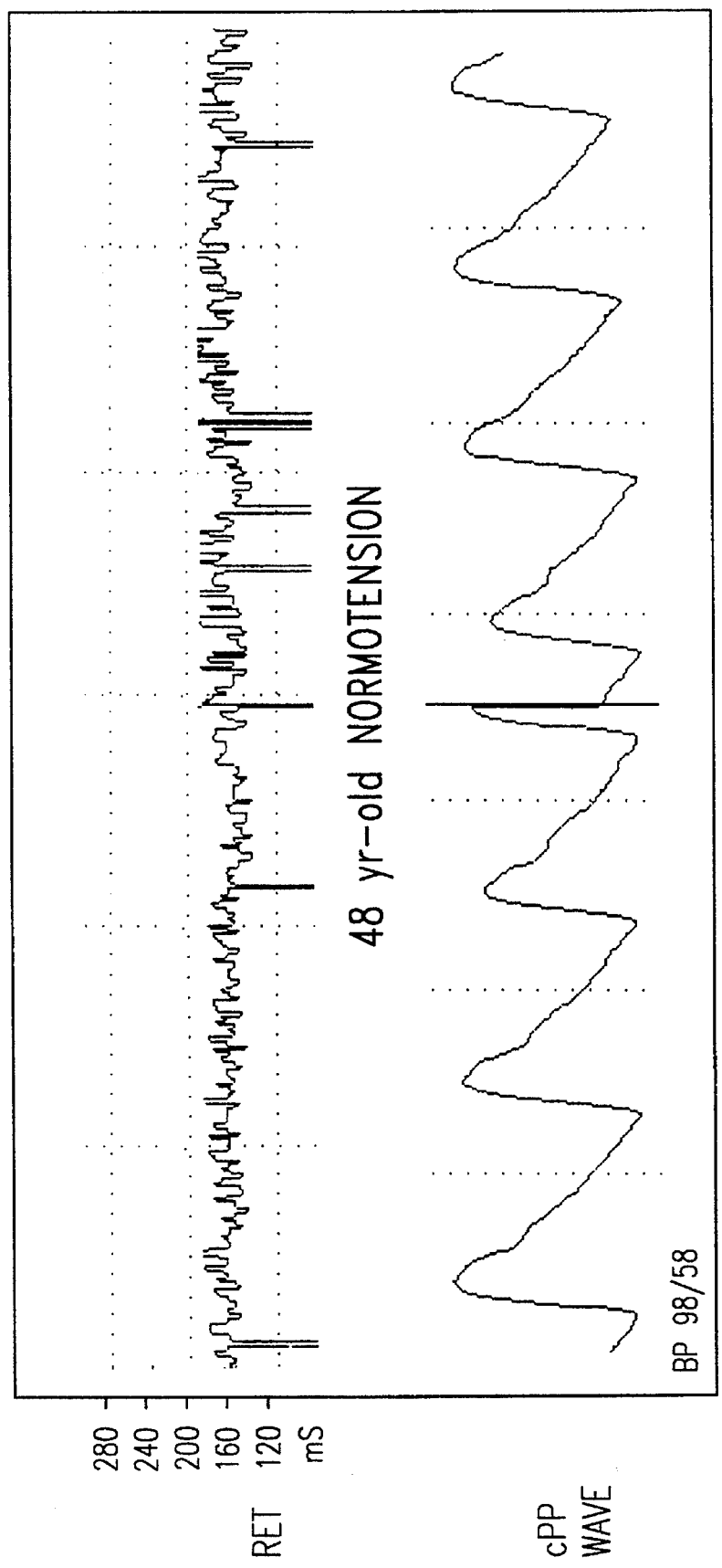
Figure 4C:
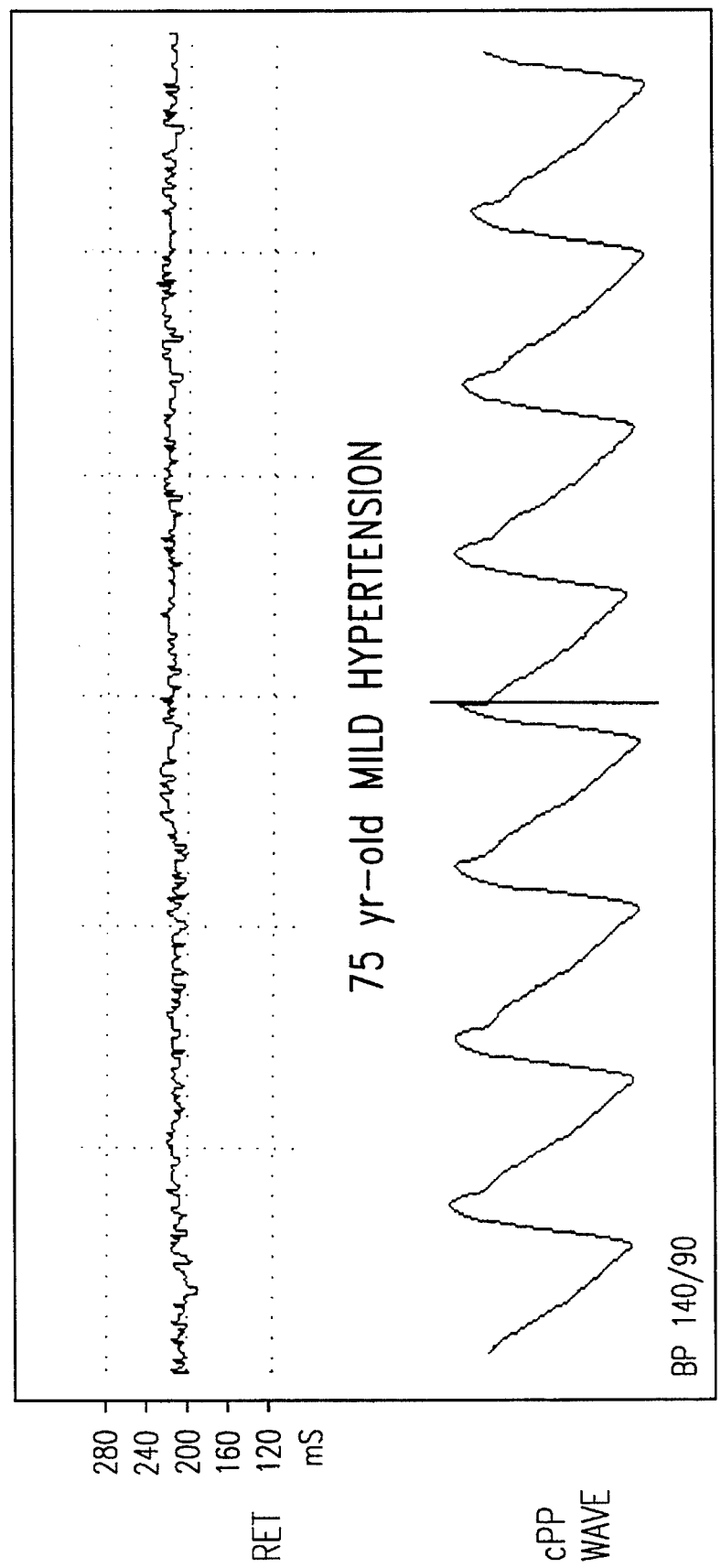
Figure 5A:
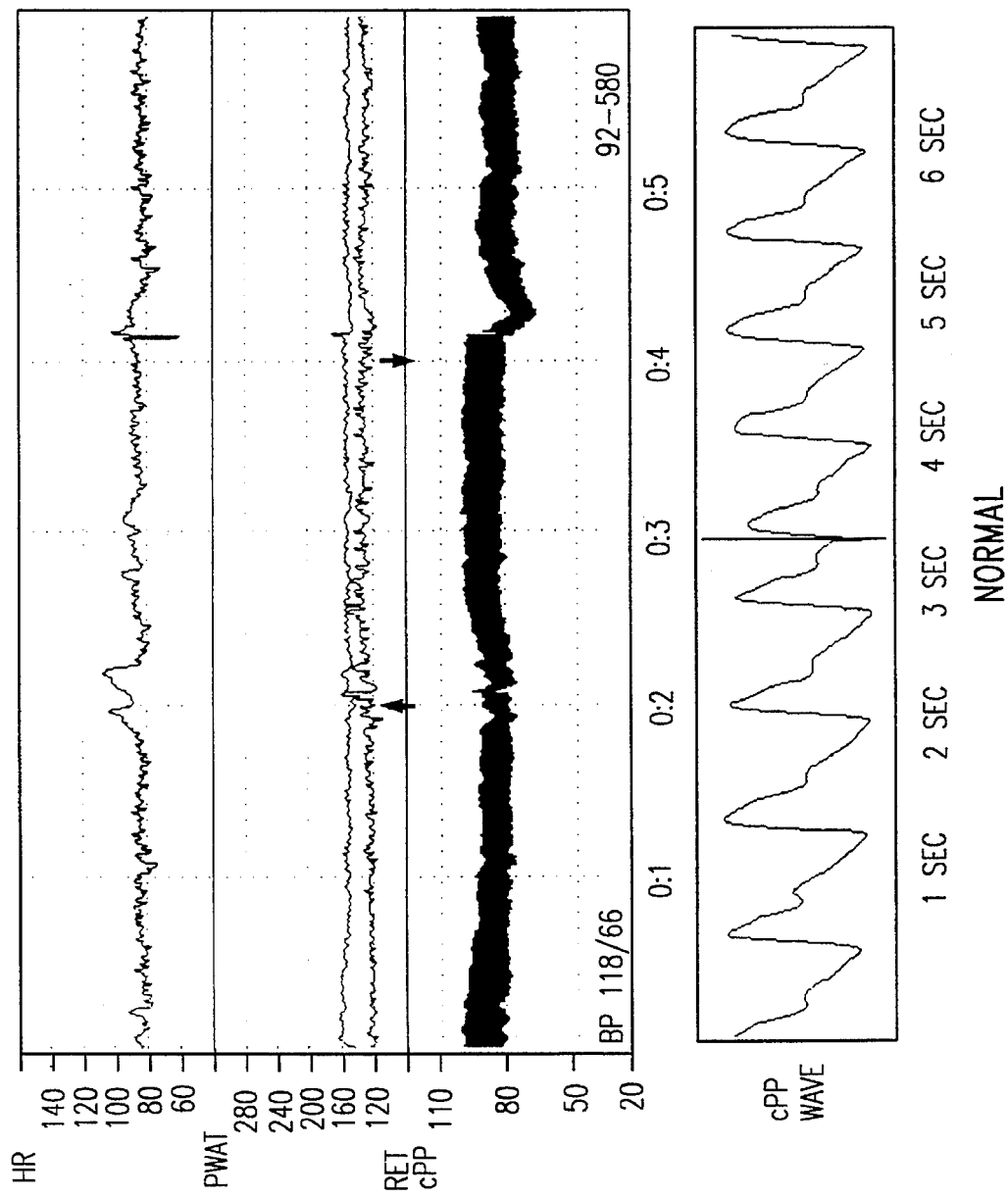
FIGS. 5A and 5B show illustrations of a postural cardiovascular test using a sit-standing-sit sequence. From the start of each record to the first (upward) arrow the patient sits then stands until the next (downward) arrow and then sits again. Each segment occupies 2 min (2 vertical dotted lines).
Figure 5B:
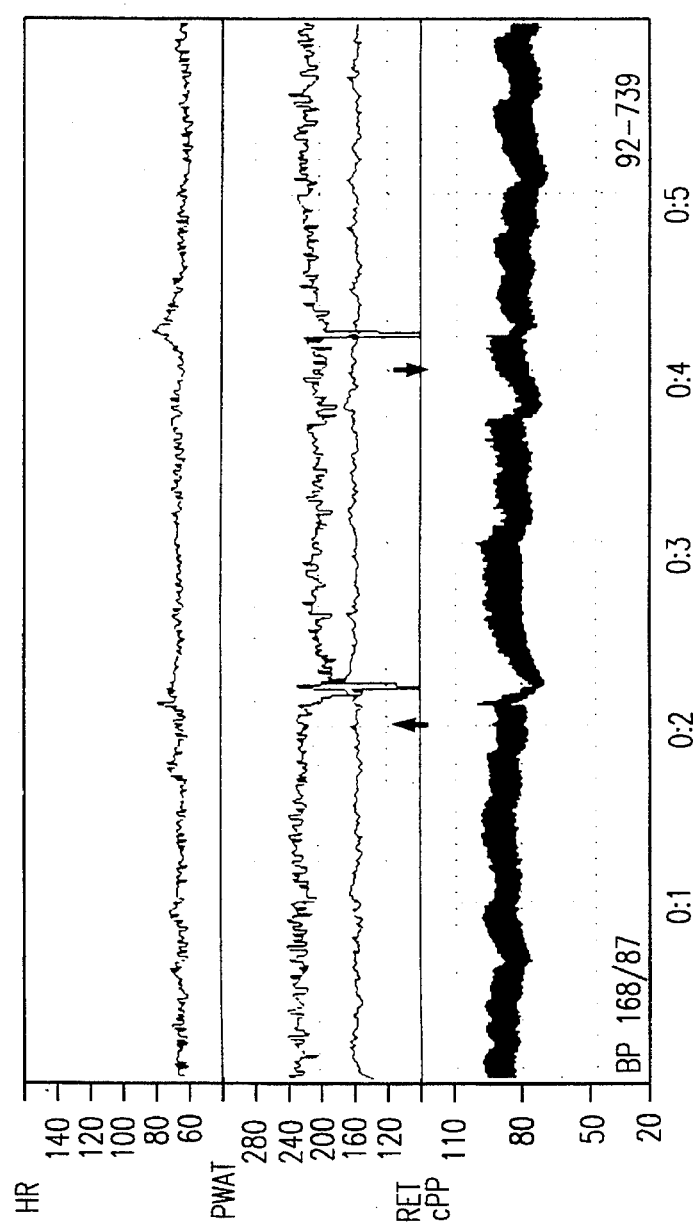

The RET and PWC records of FIGS. 4A–C illustrate how these patterns change with advancing age. The RETs are shortest in FIG. 4A, recorded from a 21-year-old patient and longest in FIG. 4C, from a 75-year-old subject. The 48-year-old patient whose record is shown in FIG. 4B has a RET of 165 mS, which lies between the previous values. These findings are consistent with the cardiologic observation that, with increasing age, there is decreasing arterial compliance. This is also shown in the PWCs. FIGS. 5A and 5B illustrate a cardiovascular (CV) test which adds HR and cPP amplitude to the other CV measurements discussed earlier. FIG. 5A shows the patterns recorded from a normotensive pregnant patient. Compared to the normal patient, the findings in the chronic hypertensive (FIG. 5B) patient are as follows:

1. The baseline HR level is lower but is within the normal range.
2. The PWAT is similar.
3. The RET is longer, about 230 mS vs. 120 mS.
4. The cPP amplitude narrows with standing.
5. The upstroke of the PWC is "bent over," so that the peak is delayed (longer RET). The downslope has lost most of the details (loss of compliance) present in the normal PWC.

FIGS. 6A and 6B show the HR, PWAT, RET, cPP patterns, and PWCs recorded from a hypertensive pregnant patient before and after the administration of a rapidly acting, short duration calciumchannel blocker (nifedipine) by the sublingual route. In FIG. 6A, 19 minutes before nifedipine was given, the RET was prolonged to 200 mS. Within 10 minutes of sublingual nifedipine administration (not illustrated) there was gradual and noticeable shortening of RET which continued on until a low point of about 140 mS at the end of FIG. 6B (23 minutes after nifedipine administration).

Decreased RET of this level continued throughout the remaining 48 minutes of the study. The blood pressure fell from 135/92 mmHg before nifedipine to 129/83 mmHg after its administration (FIG. 6B).

The similarities between PWC details of the peripheral pressure pulse and the carotid arterypulse raises the possibility that a simple, convenient, noninvasive method may be available which provides access to basic physiologic cardiovascular data. The statement of Berne and Levy that "the rapid ejection phase of systole is significantly prolonged as aortic compliance decreased" is supported by the work of Dontas and co-workers. These investigators found that the time from the foot of carotid artery pulse to its peak prolonged with increasing age (which is associated with increasing rigidity of the arterial system).

A similar finding with a peripheral pressure pulse system where RET increased with aging (FIG. 4) suggests that such a measurement could be valuable in assessing cardiovascular compliance in diseases that affect the elasticity of the vascular system, e.g., hypertension and diabetes mellitus. Under these circumstances, it may not only be of value for diagnosis, as illustrated in FIG. 5, but also for management (FIG. 6).

The PWCs illustrated in FIG. 3 are of similar technical quality to those observed in 99 percent of PWCs recorded from more than 2,500 patients (over 20,000 individual computer-generated records). The hypertensive labeling may be considered tentative at this time but seems reasonable in light of experience with the effect of postural changes, diuretics, vasodilating and/or sympatholytic drugs on PWcs. The concept of a hypervolemic-vasoconstrictive model for hypertension is also consistent with the renin hypothesis of Laragh.

What is claimed is:

1. Apparatus for measuring compliance of the arteries of a patient comprising:

means for measuring the cutaneous pressure pulse wave of the cutaneous tissue overlying a finger tip;

means for electronically recording the cutaneous pressure pulse wave;

means for measuring the ECG wave;

means for electronically recording the ECG wave;

means for determining the R-wave of the ECG wave;

means for measuring the elapsed time from the peak of the R-wave to the time of the first up slope of the cutaneous pressure pulse wave;

means for measuring the time interval from the up slope of the cutaneous pressure pulse wave to the peak of the cutaneous pressure pulse wave; and means for displaying said elapsed time and said time interval measurements.

2. Apparatus for measuring compliance of the arteries of a patient consisting of:

a noninvasive pressure transducer for measuring the cutaneous pressure pulse wave of a finger;

means for electronically recording the cutaneous pressure pulse wave;

means for measuring the ECG wave;

means for electronically recording the ECG wave; and means for measuring the duration of the up slope of the cutaneous pressure pulse wave, said duration being measured from the onset to the peak of said cutaneous pressure pulse wave.

3. The method of determining the compliance of the arteries of a patient comprising the steps of measuring the cutaneous pressure pulse wave of a finger;

electronically recording the cutaneous pressure pulse wave;

measuring the ECG wave;

electronically recording the ECG wave;

determining the R-wave of the ECG wave;

measuring the elapsed time form the peak of the R-wave to the time of the first up slope of the cutaneous pressure pulse wave;

measuring the time interval form the up slope of the cutaneous pressure pulse wave to the peak of the cutaneous pressure pulse wave; and displaying said time measurements.

4. The method of determining the compliance of the arteries of a patient comprising the steps of measuring the cutaneous pressure pulse wave of a finger;

electronically recording the cutaneous pressure pulse wave;

measuring the ECG wave;

electronically recording the ECG wave;

determining the R-wave of the ECG wave;

measuring the time interval from the up slope of the cutaneous pressure pulse wave to the peak of the cutaneous pressure pulse wave; and displaying said time measurement.

* * * * *